United States Patent [19]
Moretz et al.

[11] Patent Number: 5,385,502
[45] Date of Patent: Jan. 31, 1995

[54] MOISTURE MANAGING BRASSIERE FOR SPORTS AND GENERAL WEAR

[75] Inventors: Herbert L. Moretz, Davidson, N.C.; Daniel L. Brier, Key Largo, Fla.

[73] Assignee: Intelpro Corporation, Lincolnton, N.C.

[21] Appl. No.: 72,522

[22] Filed: Jun. 4, 1993

Related U.S. Application Data

[63] Continuation-in-part of Ser. No. 3,263, Jan. 12, 1993, Pat. No. 5,269,720, which is a continuation-in-part of Ser. No. 991,761, Dec. 17, 1992, Pat. No. 5,297,296, which is a continuation-in-part of Ser. No. 945,677, Sep. 16, 1992, Pat. No. 5,291,617, which is a continuation-in-part of Ser. No. 842,224, Feb. 26, 1992, Pat. No. 5,210,882, which is a continuation-in-part of Ser. No. 791,066, Nov. 12, 1991, Pat. No. 5,217,782.

[51] Int. Cl.$^6$ .............................................. A41C 3/00
[52] U.S. Cl. ................................... 450/93; 450/36; 450/37; 450/30; 450/31; 450/32; 450/58; 450/61; 2/73
[58] Field of Search ................. 450/36, 37, 30, 31, 450/32, 58, 61, 93; 2/73

[56] References Cited

U.S. PATENT DOCUMENTS

| | | |
|---|---|---|
| 3,203,424 | 8/1965 | Garutso . |
| 3,237,625 | 3/1966 | Johnson . |
| 3,613,687 | 10/1971 | Kennedy . |
| 3,706,103 | 12/1972 | Senser . |
| 3,852,828 | 12/1974 | Silverstein . |
| 4,309,024 | 6/1983 | Williams . |
| 4,640,287 | 2/1987 | Anderson et al. . |
| 4,880,424 | 11/1989 | Rautenberg . |
| 4,961,419 | 10/1990 | Tribble et al. . |
| 5,022,887 | 6/1991 | Lawson ................................. 450/32 |
| 5,037,409 | 8/1991 | Chen et al. . |
| 5,149,336 | 9/1992 | Clarke et al. . |
| 5,269,720 | 12/1993 | Moretz et al. ........................ 450/37 |

FOREIGN PATENT DOCUMENTS 327823  8/1989  European Pat. Off. .

OTHER PUBLICATIONS

The Sign of Winners, Published by: Akzo Fibres and Polymers division, undated.
Hydrolfil Nylon, by Allied SIgnal, 1988.
Industrial Fabric Opportunities for Hydrophilic Nylons, by Judy Peters, Gordon and Breach Science Publishers, from Polymers News, 1990, vol. 15, pp. 238-244.

Primary Examiner—Clifford D. Crowder
Assistant Examiner—Gloria Hale
Attorney, Agent, or Firm—W. Thad Adams, III

[57] ABSTRACT

A moisture managing brassiere for sports wear and general wear includes a front portion, a back portion connected to the front portion, and a pair of shoulder straps connected respectively at one end to the front portion and at respective opposite ends to the back portion. The brassiere is constructed of a composite stretch fabric including an inner fabric layer, and intermediate fabric layer, and an outer shell fabric layer. The inner fabric layer is constructed of hydrophobic moisture wicking fibers for residing in skin contact during garment wear. The intermediate fabric layer resides adjacent to the inner fabric layer for receiving, dispersing, and transporting moisture outwardly away from the inner fabric layer. The outer fabric layer resides adjacent to the intermediate fabric layer for receiving and dispersing moisture wicked outwardly from the inner and intermediate fabric layers.

6 Claims, 4 Drawing Sheets

MOISTURE MANAGING BRASSIERE FOR SPORTS AND GENERAL WEAR

TECHNICAL FIELD AND BACKGROUND OF THE INVENTION

This application is a continuation-in-part of application Ser. No. 003,263 filed Jan. 12, 1993, (U.S. Pat. No. 5,269,720, which is a continuation-in-part of application Ser. No. 991,761 filed Dec. 17, 1992, U.S. Pat. No. 5,297,296 which is a continuation-in-part of application Ser. No. 945,677, U.S. Pat. No. 5,291,617 filed Sep. 16, 1992 which is a continuation-in-part of application Ser. No. 842,224 filed Feb. 26, 1992 (U.S. Pat. No. 5,210,882) which is a continuation-in-part of application Ser. No. 791,066 filed Nov. 12, 1991 (Pat. No. 5,217,782).

The invention relates to a moisture managing brassiere for sports wear and general wear. The brassiere includes a composite moisture management fabric with spandex yarns incorporated into the outer shell fabric of the brassiere for providing added support strength and comfort to the wearer. The added support, coupled with the moisture control, are desirable characteristics of a brassiere for the athletic woman. The brassiere of the present invention satisfies this criteria by creating a sports bra that effectively handles perspiration and creates a drier environment for the breasts.

A brassiere with adequate support strength is more comfortable for wear and reduces the risk of injury to the breast during periods of recreation and exercise. Prior art sports brassieres include such features for providing additional support to the breasts. These bras, however, do not include a means for effectively moving moisture away from the skin as the body naturally perspires.

During active periods, moisture perspiration tends to accumulate in an area directly beneath the breasts and between the breasts. Additionally, moisture tends to gather in the lower back portion of the brassiere. This creates a generally wet and uncomfortable environment against the skin, which can promote bacteria and fungus growth. The brassiere of the present invention includes a means for effectively handling this moisture by quickly moving it from the skin, and ultimately to the atmosphere.

The brassiere of the present invention is also suited for general, everyday wear. Women's breasts naturally perspire throughout the day, even during times of relatively light activity. Accordingly, this invention can be worn to help transport moisture from the skin to an area of the brassiere where it can be more easily evaporated. This creates a drier, more comfortable, and more healthful environment for the breasts.

SUMMARY OF THE INVENTION

Therefore, it is an object of the invention to provide a moisture managing brassiere for sports and general wear, and including provisions for moisture dissipation and added support strength.

It is another object of the invention to provide a brassiere which includes moisture transport inserts positioned in areas of the brassiere where perspiration is typically the greatest, to thereby more effectively remove moisture from the skin.

It is another object of the invention to provide a brassiere which includes elastic or spandex yarns incorporated in the shell fabric of the brassiere for providing added support to the breasts of the wearer.

These and other objects of the present invention are achieved in the preferred embodiments disclosed below by providing a moisture managing brassiere having a breast supporting front portion, a back portion connected to the front portion, and a pair of shoulder straps connected respectively at one end to the front portion and at respective opposite ends to the back portion.

The brassiere is constructed of a composite stretch fabric including an inner fabric layer, an intermediate fabric layer, and an outer shell fabric layer. The inner fabric layer is constructed of hydrophobic moisture wicking fibers for residing in skin contact during garment wear and for wicking moisture away from the skin of the wearer. The intermediate fabric layer resides adjacent to the inner fabric layer for receiving, dispersing, and transporting moisture outwardly away from the inner fabric layer. The outer fabric layer resides adjacent to the intermediate fabric layer for receiving and dispersing moisture wicked outwardly from the inner and intermediate fabric layers. The outer fabric layer comprises the outer shell fabric of the brassiere.

According to one preferred embodiment of the invention, the inner fabric layer includes a single-component fabric constructed of hydrophobic polyester yarns formed of fibers having a high surface area in relation to volume.

According to another preferred embodiment of the invention, the inner fabric layer includes an integrally knit bi-component fabric constructed of hydrophobic polyester fibers on an innermost fabric face next to the skin of the wearer, and hydrophilic nylon on an obverse fabric face away from the skin of the wearer.

According to yet another preferred embodiment of the invention, the inner fabric layer includes an integrally knit tri-component fabric constructed of hydrophobic polyester fibers on an innermost fabric face next to the skin of the wearer, a first hydrophilic nylon component residing adjacent to the hydrophobic polyester fibers and away from the skin of the wearer, and a second hydrophilic nylon component residing adjacent to the first hydrophilic nylon component and comprising an outermost fabric face of the tri-component fabric.

Preferably, the second hydrophilic nylon component has a brushed fabric face for enhancing the ability of the second nylon component to disperse moisture moved outwardly from the first nylon component.

According to one preferred embodiment of the invention, the intermediate fabric layer comprises first and second moisture transport inserts located in a lower front portion of the brassiere for residing generally beneath respective breasts of the wearer.

According to another preferred embodiment of the invention, the intermediate fabric layer comprises a moisture transport insert having a continuous area of moisture transporting fabric located in a lower front portion of the brassiere, said insert residing generally beneath the breasts of the wearer and extending laterally from one breast to the other breast during garment wear.

According to yet another preferred embodiment of the invention, the intermediate fabric layer comprises a moisture transport insert having a continuous area of moisture transport fabric located in a front center portion of the brassiere and in a lower front portion of the brassiere, said insert residing generally in the cleavage area of the wearer and beneath the breasts of the wearer extending laterally from one breast to the other breast during garment wear.

According to yet another preferred embodiment of the invention, the intermediate fabric layer comprises a moisture transport insert residing in the lower back portion of the brassiere and extending laterally from one side of the back portion to the other side of the back portion.

Preferably, the hydrophobic yarn of the inner fabric layer is chosen from the fiber group consisting of polyester and polypropylene.

Preferably, the intermediate fabric layer is constructed of yarns chosen from the fiber group consisting of rayon, polyester, cotton, and a blend of polyester and cotton.

Preferably, the outer fabric layer includes elastic yarns incorporated therein for providing added stretch and support strength to the brassiere.

According to yet another preferred embodiment of the invention, the front portion of the brassiere includes a pair of brassiere cups for holding and supporting the breasts of the wearer.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
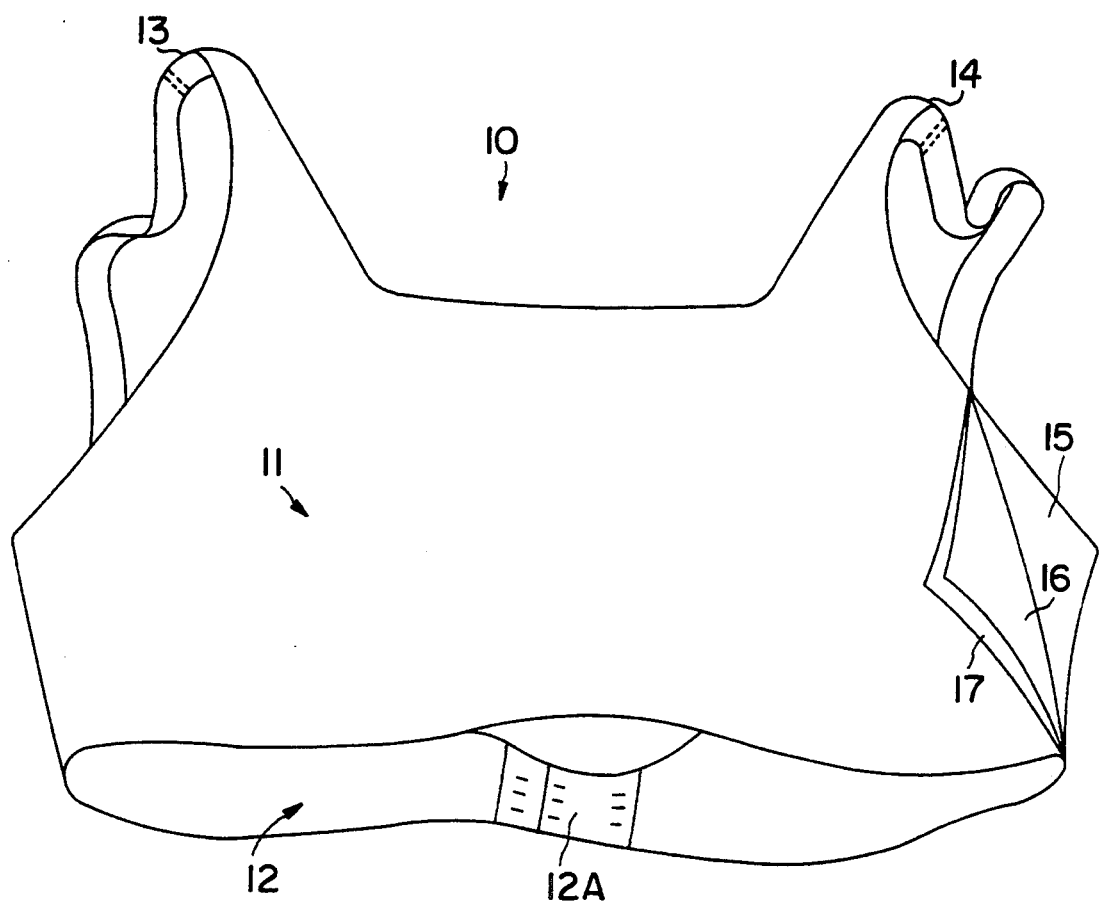
FIG. 1 is a moisture managing brassiere according to one embodiment of the invention particularly suited for sports wear.

Referring now specifically to the drawings, a moisture managing brassiere according to a preferred embodiment of the present invention is shown in FIG. 1, and broadly indicated at reference numeral 10. Because of its enhanced support and moisture management characteristics, the brassiere 10 is particularly suited for active wear or sports wear. However, the fabric composite of the brassiere 10 may be included in a brassiere for general wear for maintaining a drier environment next to the skin of the wearer.

As shown in FIG. 1, the brassiere 10 includes a breast supporting, undivided front portion 11, a back portion 12 connected to the front portion 11, and a pair of shoulder straps 13 and 14. Each of the pairs of shoulder straps 13 and 14 are preferably formed with and extend from the respective front and back portions 11 and 12 of the brassiere 10. Preferably, the respective free ends of each of the pairs of shoulder straps 13 and 14 are sewn together at the top of the straps. The front and back portions 11 and 12 are preferably connected along respective sides using a conventional stitch technique. Other means well known in the art for connecting the shoulder straps and front and back portions of the brassiere may be substituted without departing from the scope of the invention.

The back portion 12 may include an attachment means 12A, such as a hook and eye, for allowing the wearer to conveniently put-on and remove the garment. According to another embodiment, the back portion does not include an attachment means. Instead, the garment is put-on and removed by simply pulling the garment over the head and passing the arms through the respective straps 13 and 14.

The brassiere 10 is constructed of a multi-layer composite fabric having an inner moisture wicking fabric layer 15 formed of hydrophobic yarns; an intermediate moisture dispersal fabric layer 16 formed of hydrophilic yarns; and an outer shell fabric layer 17. Preferably, the outer shell fabric 17 includes elastic yarns incorporated therein for providing added support strength to the garment and added comfort to the breasts during periods of heavy activity. Preferably, the garment is constructed of a warp-knitted material. Each layer is suitably attached to the other by conventional sewing techniques, or by fusing.

The inner fabric layer 15 is intended to wick moisture away from the skin. It does not absorb moisture. Preferably, the inner fabric layer 15 is formed of polyester wicking fibers, such as the "Coolmax" or "Thermax" fibers manufactured by DuPont Corporation. "Coolmax" polyester fibers have a relatively high surface area in relation to volume, with channels running longitudinally along the shaft of the fiber to enhance the wicking or transport of moisture. Such fibers are designed specifically to move or wick moisture, and may be chemically treated to further enhance such ability. The "Thermax" fibers may be used in a brassiere for wear during periods of colder weather, and the "Coolmax" fibers may be used in brassieres designed for warmer weather wear. According to another embodiment, polypropylene fibers or specially treated nylon fibers may be substituted for the polyester fibers for attaining a similar wicking effect.

Figure 2:
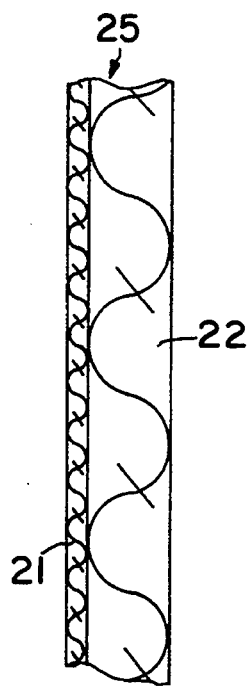
FIG. 2 is an enlarged and exaggerated cross-sectional view of a bi-component knit fabric that integrates hydrophobic fibers and hydrophilic fibers according to an embodiment of the invention.

FIG. 2 shows a cross-sectional view of a second embodiment of the inner fabric layer 25. The layer 25 comprises a "push-pull" bi-component warp knit fabric formed of hydrophobic polyester wicking fibers and hydrophilic fibers. The polyester wicking fibers form the innermost fabric face 21 for residing next to the skin of the wearer. The hydrophilic fibers, such as the "Hydrofil" brand fibers produced by Allied Fibers, are integrally knit to the polyester wicking fibers and form the obverse fabric face 22.

Figure 3:
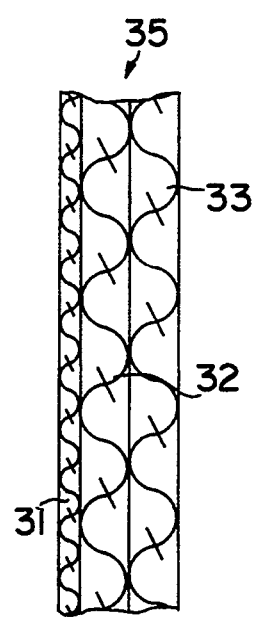
FIG. 3 is an enlarged and exaggerated cross-sectional view of a tri-component knit fabric that integrates hydrophobic fibers and hydrophilic fibers according to another embodiment of the invention.

According to a third embodiment shown in FIG. 3, the inner fabric layer 35 is constructed of a tri-component fabric. This fabric includes the integrated "push-pull" hydrophobic/hydrophilic construction of the hi-component fabric with the addition of a second integrally knit hydrophilic component 33. The second hydrophilic component 33 is preferably a hydrophilic nylon, such as "Hydrofil," and includes a brushed or sanded fabric face. The brushed or sanded face helps to further disperse moisture wicked outwardly from the skin by the hydrophobic wicking fibers of the first fabric face 31.

Referring again to FIG. 1, the intermediate moisture dispersal fabric layer 16 of the brassiere 10 is positioned between the inner fabric layer 15 and the outer shell fabric layer 17. According to one embodiment, the layer 16 is included throughout the entire fabric surface area of the brassiere 10. Preferably, the intermediate fabric layer 16 is formed of hydrophilic yarns which operate to receive, disperse, and transport moisture from the inner moisture wicking fabric layer 15 to the outer shell fabric layer 17. The hydrophilic yarn may be hydrophilic nylon, cotton, rayon and blends of hydrophilic nylon and conventional nylon.

The outer shell fabric layer 17 forms the outermost fabric layer of the brassiere 10. This fabric layer 17 is preferably constructed of hydrophilic yarns such as cotton, rayon, and hydrophilic nylon. However, other conventional hydrophilic or hydrophobic yarns may be substituted as desired. Additionally, the outer shell fabric layer 17 includes elastic yarns, or spandex, for providing added stretch and support strength to the brassiere. This results in greater comfort to breasts during particularly periods of heavy exercise. Because of the added support strength, the brassiere 10 is especially suited for active wear or sports wear.

Figure 4:
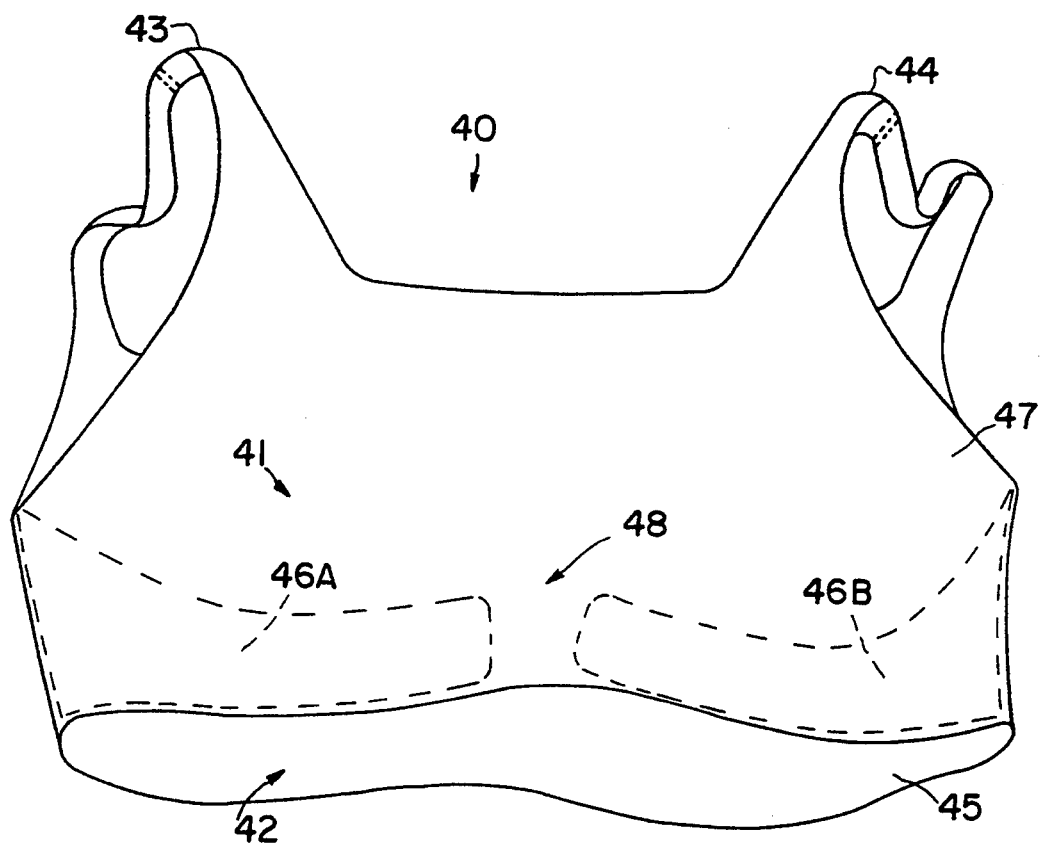
FIG. 4 is a moisture managing brassiere according to another embodiment of the invention showing first and second moisture transport inserts residing in a lower front portion of the brassiere.

According to another embodiment shown in FIG. 4, a brassiere 40 includes a front portion 41, a back portion 42, and a pair of shoulder straps 43 and 44. The means for attaching the components of the brassiere 40 are identical to that described above with reference to brassiere 10.

The brassiere 40 is constructed of a multi-layer composite fabric having an inner fabric layer 45, a pair of moisture transport inserts 46A and 46B comprising an intermediate fabric layer, and an outer shell fabric layer 47. As described above with reference to brassiere 10, the inner fabric layer 45 is preferably constructed of hydrophobic yarns, and may comprise a bi-component or tri-component fabric previously described. The outer shell fabric layer 47 is constructed of a suitable hydrophilic or hydrophobic yarn. Preferably, the outer shell fabric layer 47 further includes elastic yarns or spandex incorporated therein for providing added support strength to the garment and added comfort to the wearer.

The intermediate moisture transport inserts 46A and 46B comprise the intermediate fabric layer of the brassiere 40, and are preferably constructed of hydrophilic yarns for receiving, dispersing, and transporting moisture from the inner moisture wicking fabric layer 45 to the outer shell fabric layer 47. Preferably, the hydrophilic fibers comprise hydrophilic nylon which may be chemically treated to enhance its ability to move or transport moisture against the natural pull of gravity. The Intera Corporation and Millikan Corporation are currently utilizing respective processes for chemically treating such fibers. Chemically treated hydrophobic yarns may also be used for achieving a similar effect.

Each of the moisture transport inserts 46A and 46B are located between the inner fabric layer 45 and the outer shell fabric layer 47 residing generally in a lower front portion 48 of the brassiere 40, and beneath respective breasts of the wearer during garment wear. Preferably, the moisture transport inserts 46A and 46B are sewn to the inner fabric layer 45 using a conventional stitch technique.

Figure 5:
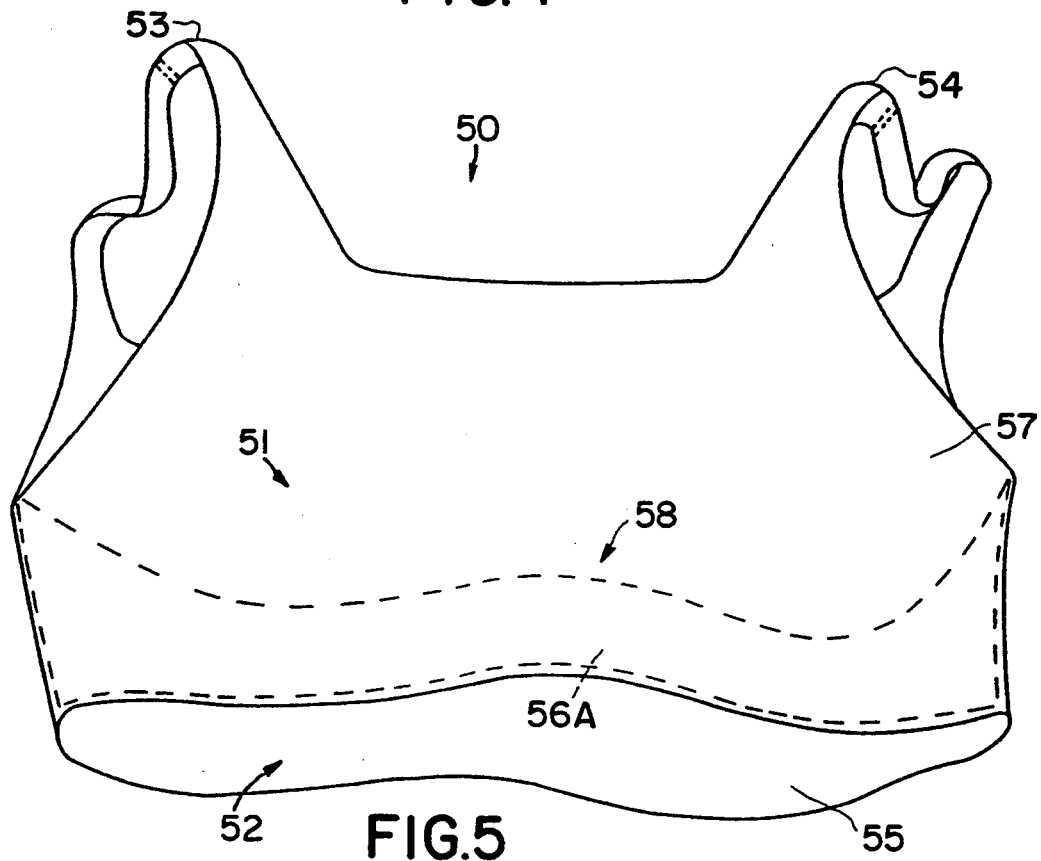
FIG. 5 is a moisture managing brassiere according to another embodiment of the invention showing a single moisture transport insert residing in a lower front portion of the brassiere.

According to another embodiment illustrated in FIG. 5, a brassiere 50 includes a front portion 51, a back portion 52, and a pair of shoulder straps 53 and 54. The means for attaching the components of the brassiere 50 are identical to that described above with reference to brassiere 10.

The brassiere 50 is constructed of a multi-layer fabric comprising an inner fabric layer 55, a single moisture transport insert 56A comprising an intermediate fabric layer, and an outer shell fabric layer 57. The fabric construction of the inner and outer fabric layers 55 and 57 is identical to the inner and outer fabric layers 15 and 17 as described above with reference to brassiere 10.

The moisture transport insert 56A comprises a single continuous section of moisture transporting fabric, and is located in a lower front portion 58 of the brassiere 50. The moisture transport insert 56A is designed to reside generally beneath the breasts of the wearer, and to extend from beneath one breast to beneath the other breast during garment wear as shown in FIG. 5. Like inserts 46A and 46B of brassiere 40, the moisture transport insert 56A of brassiere 50 is preferably constructed of hydrophilic yarns such as hydrophilic nylon, cotton, rayon and blends of hydrophilic nylon and conventional nylon. The moisture transport insert 56A is located between the inner fabric layer 55 and the outer shell fabric layer 57, and is preferably sewn to the inner fabric layer 55 using a conventional stitch technique.

Figure 6:
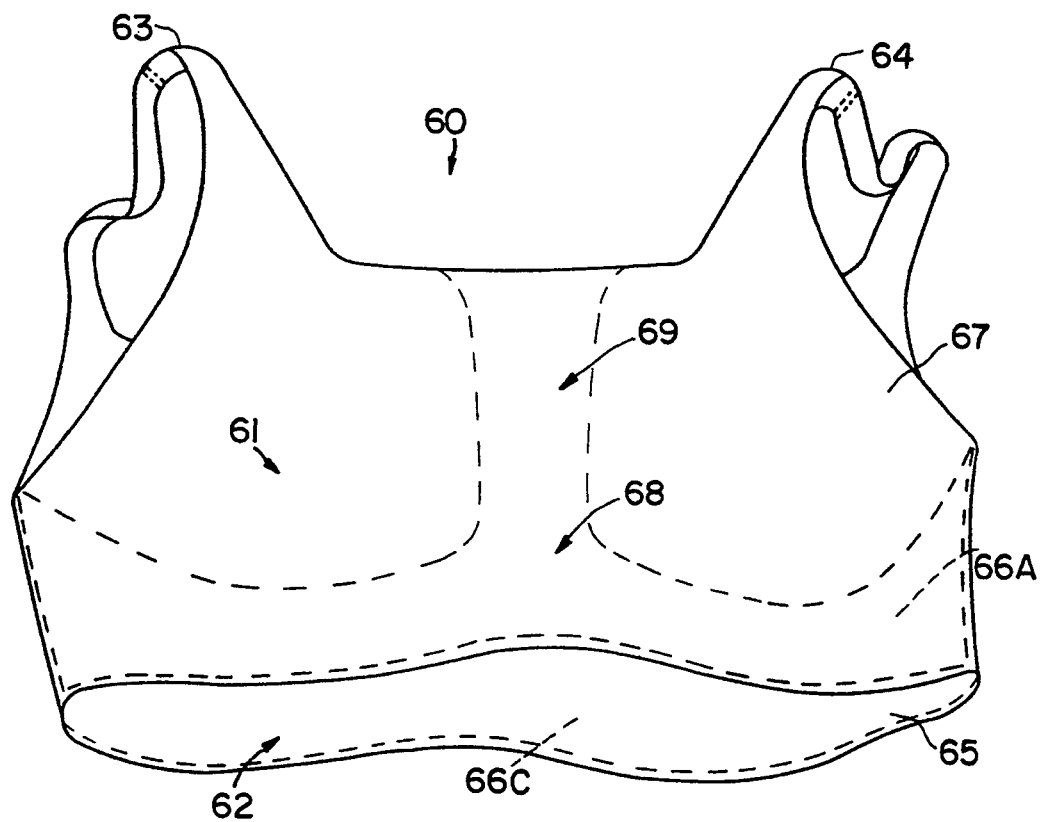
FIG. 6 is a moisture managing brassiere according to another embodiment of the invention showing a single moisture transport insert residing in a lower front portion and center front portion of the brassiere.

According to yet another embodiment shown in FIG. 6, a brassiere 60 includes a front portion 61, a back portion 62, and a pair of shoulder straps 63 and 64. The means for attaching the components of the brassiere 60 are identical to that described above with reference to brassiere 10.

The brassiere 60 is constructed of a multi-layer fabric comprising an inner fabric layer 65, first and second moisture transport inserts 66A and 66C comprising an intermediate fabric layer, and an outer shell fabric layer 67. The fabric construction of the inner and outer fabric layers 65 and 67 is identical to that described with reference to the inner and outer fabric layers 15 and 17 of the brassiere 10.

Figure 7:
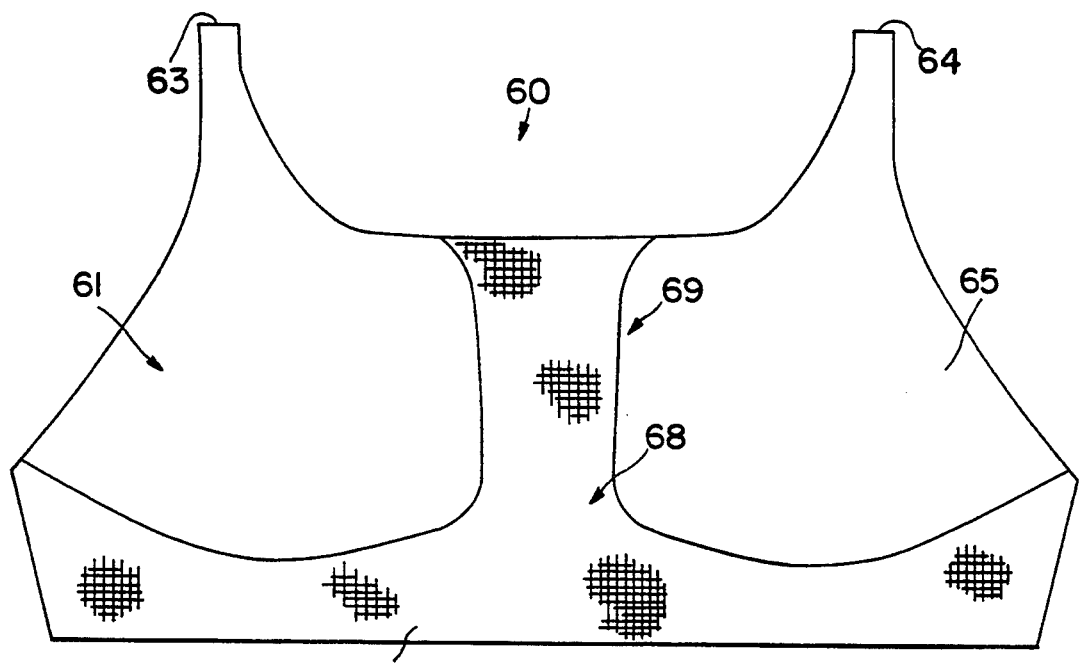
FIG. 7 is a view of the inside of the front portion of the brassiere illustrated in FIG. 6.

As shown in FIGS. 6 and 7, the first moisture transport insert 66A is located in a lower front portion 68 and a front center portion 69 of the brassiere 60 to form a single, continuous section of moisture transporting fabric. However, the moisture transport insert 66A may be divided into two or more sections (not shown) for residing respectively beneath the breast of the wearer and between the breasts. During garment wear, the moisture transport insert 66A is designed to extend from beneath one breast of the wearer to beneath the other breast, and in the cleavage area between the breasts. The moisture transport insert 66A cooperates with the inner and outer fabric layers 65 and 67 to transport and disperse a maximum amount of moisture away from the skin of the wearer in areas of the brassiere 60 where perspiration tends to gather and accumulate. FIG. 7 illustrates an the brassiere 60 turned inside out.

Figure 8:
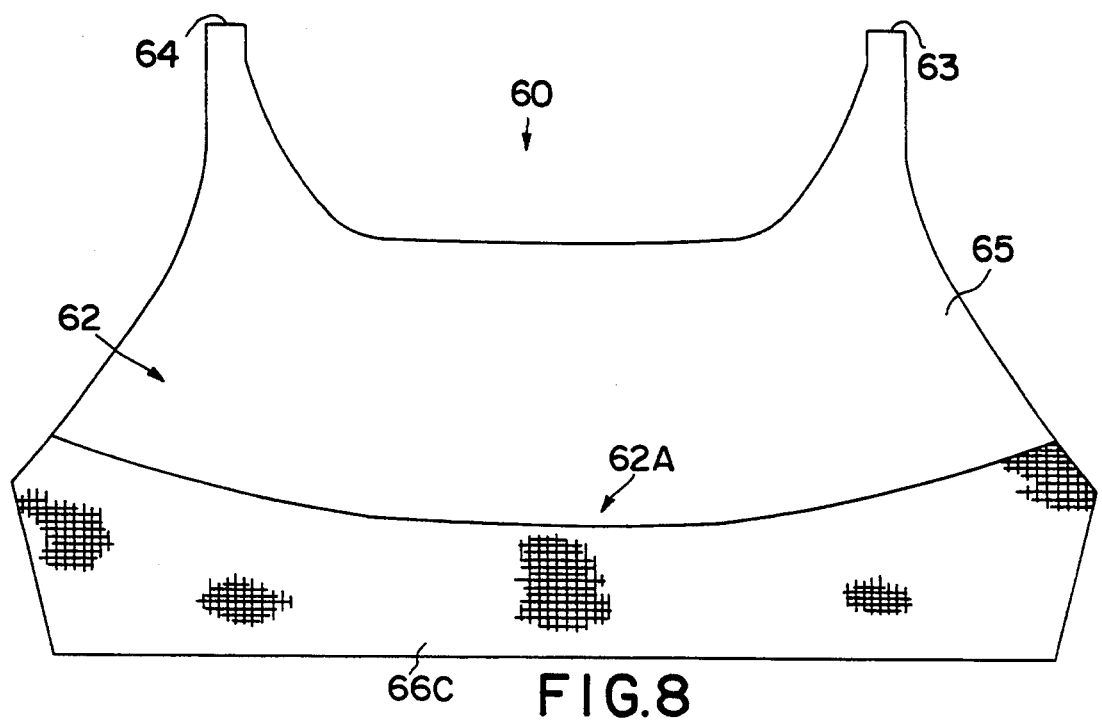
FIG. 8 is a view of the inside of the back portion of the brassiere illustrated in FIGS. 6 and 7.

As shown in FIG. 8, the second moisture transport insert 66C of the brassiere 60 resides in a lower back portion 62A of the brassiere 60. The second moisture transport insert 66C is positioned between the inner fabric layer 65 and the outer shell fabric layer 67, and extends laterally from one side of the back portion 62 to the other side of the back portion 62 for moving moisture away from the back of the wearer. Since moisture tends to accumulate in the lower back portion 62A of the brassiere 60, the moisture transport insert 66C operates to effectively move this moisture outwardly away from the skin and upwardly to a drier section of the back portion 62 to enhance evaporation. Additionally, the moisture transport insert 66C may be included in each of the brassiere embodiments 10, 40, and 50 described above for added moisture management in the back portion of the garment.

Like the inserts previously described, the moisture transport inserts 66A and 66C of brassiere 60 are preferably constructed of hydrophilic yarns such as hydrophilic nylon, cotton, rayon and blends of hydrophilic nylon and conventional nylon. The moisture transport inserts 66A and 66C are located between the inner fabric layer 65 and the outer shell fabric layer 67, and are preferably sewn to the inner fabric layer 65 using a conventional stitch technique.

Figure 9:
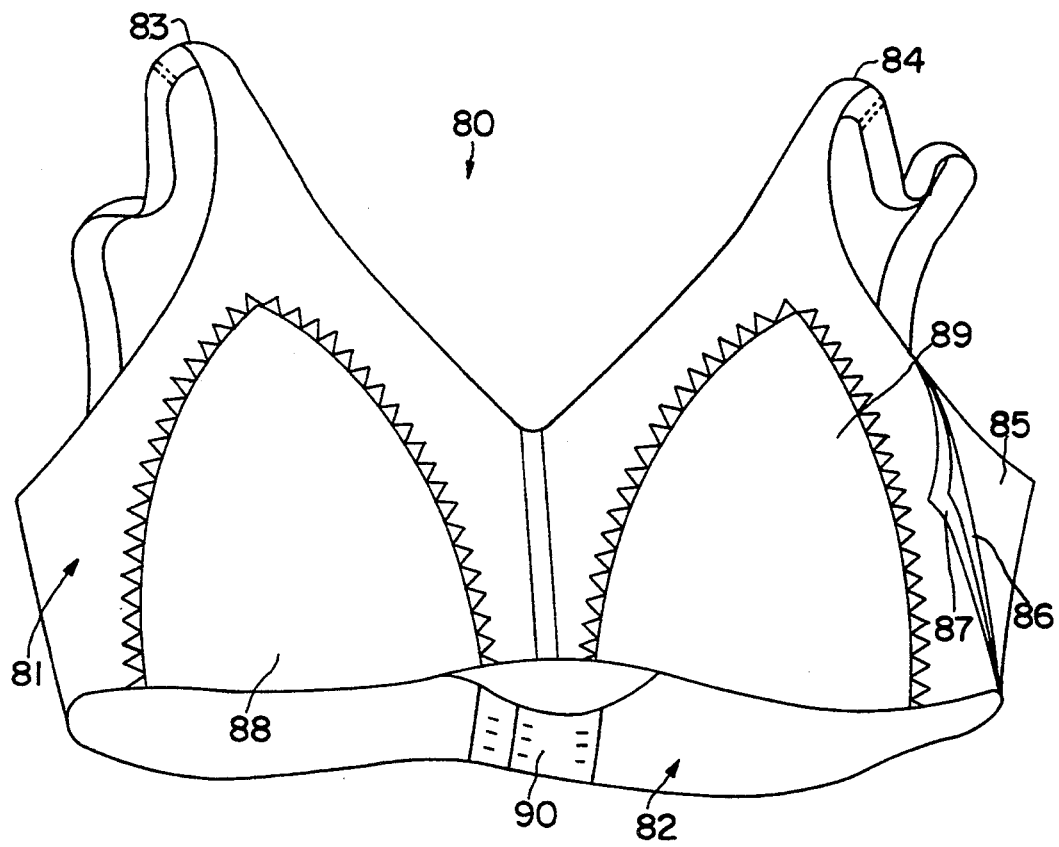
FIG. 9 is a moisture managing brassiere according to another embodiment of the invention particularly suited for general wear.

According to the embodiment shown in FIG. 9, a brassiere 80 includes a front portion 81, a back portion 82, and a pair of shoulder straps 83 and 84. The front portion 81 includes a pair of brassiere cups 88 and 89 for holding and supporting the breasts of the wearer. Preferably, the back portion 82 includes an attachment means 90 for conveniently putting-on and removing the garment. The brassiere 80 of this embodiment is particularly suited for general wear.

The fabric construction of the inner, intermediate, and outer fabric layers 85, 86, and 87 is identical to that described above with reference to the inner, intermediate, and outer fabric layers 15, 16, and 17 of the brassiere 10.

A moisture managing brassiere is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. A moisture managing brassiere having a breast supporting front portion, a back portion connected to said front portion, and a pair of shoulder straps connected respectively at one end to said front portion and at respective opposite ends to said back portion, said brassiere constructed of a composite stretch fabric comprising:
   (a) an inner fabric layer constructed of hydrophobic moisture wicking fibers for residing in skin contact during garment wear and for wicking moisture away from the skin of the wearer;
   (b) an intermediate fabric layer residing adjacent to said inner fabric layer for receiving, dispersing, and transporting moisture outwardly away from said inner fabric layer; and
   (c) an outer fabric layer residing adjacent said intermediate fabric layer for receiving and dispersing moisture wicked outwardly from said inner and intermediate fabric layers, said outer fabric layer comprising the outer shell fabric of said brassiere.

2. A brassiere according to claim 1, wherein said inner fabric layer comprises a single-component fabric constructed of hydrophobic polyester yarns formed of fibers having a high surface area in relation to volume.

3. A brassiere according to claim 1, wherein the hydrophobic yarn of said inner fabric layer is chosen from the fiber group consisting of polyester and polypropylene.

4. A brassiere according to claim 1, wherein said intermediate fabric layer is constructed of yarns chosen from the fiber group consisting of rayon, polyester, cotton, and a blend of polyester and cotton.

5. A brassiere according to claim 1, wherein said outer fabric layer includes elastic yarns incorporated therein for providing added stretch and support strength to the brassiere.

6. A brassiere according to claim 1, wherein the front portion of said brassiere includes a pair of brassiere cups for holding and supporting the breasts of the wearer.

* * * * *